United States Patent
Loebach

Patent Number: 5,284,054
Date of Patent: Feb. 8, 1994

[54] METHOD AND APPARATUS FOR PREPARING A GAS MIXTURE FOR PURPOSES OF ANALYSIS AND APPLICATION OF THE METHOD

[76] Inventor: Ernst Loebach, Tonagass 374, 9492 Eschen, Fed. Rep. of Germany

[21] Appl. No.: 835,466
[22] PCT Filed: Sep. 4, 1990
[86] PCT No.: PCT/EP90/01479
  § 371 Date: Feb. 28, 1992
  § 102(e) Date: Feb. 28, 1992
[87] PCT Pub. No.: WO91/03719
  PCT Pub. Date: Mar. 21, 1991

[30] Foreign Application Priority Data
  Sep. 4, 1989 [CH] Switzerland .......... 3203/89

[51] Int. Cl.$^5$ .......... G01N 1/22; G01N 33/497
[52] U.S. Cl. .......... 73/23.3; 73/31.7; 128/719
[58] Field of Search .......... 73/23.3, 31.02, 31.07; 128/730, 719

[56] References Cited
U.S. PATENT DOCUMENTS
4,327,575 5/1982 Locker .......... 73/31.02
4,759,210 7/1988 Wohltjen .......... 73/31.07

FOREIGN PATENT DOCUMENTS
0272507 6/1988 European Pat. Off. .......... 73/23.3
73863 9/1960 France.
1080995 8/1967 United Kingdom .......... 73/23.3
1083058 9/1967 United Kingdom .......... 73/23.3

OTHER PUBLICATIONS

"Prufrohrchen MeBtechnik", K. Leichnitz, Jun., 1981, p. 5, 24–29, 48 and 49).
"Organische Chemie", Hans Rudolf Christen et al., 1988, pp. 54 and 55.
"Methoden Der Organischen Chemie", Eugen Muller, 1953, pp. 31–41.

*Primary Examiner*—Hezron E. Williams
*Assistant Examiner*—Joseph W. Roskos
*Attorney, Agent, or Firm*—Walter C. Farley

[57] ABSTRACT

Process and device for preparing for analysis a gas mixture consisting of at least two components. The gas mixture is passed through at least two adsorption beds (3', 4'). At least one adsorption bed loaded with at least one constituent is fitted in a desorption device located upstream of the inlet system of an analyzer unit in which the constituent(s) are desorbed by lowering the pressure and/or raising the temperature.

24 Claims, 6 Drawing Sheets

METHOD AND APPARATUS FOR PREPARING A GAS MIXTURE FOR PURPOSES OF ANALYSIS AND APPLICATION OF THE METHOD

FIELD OF THE INVENTION

This invention relates to a method of preparing a gas mixture such as exhaled human or animal breath for subsequent analysis and to an apparatus for preparing this preparation.

BACKGROUND OF THE INVENTION

Analysis of a gas mixture is facilitated when the mixture is separated into various fractions before analysis proper. Illustratively a sample of respiratory air is prepared for mass-spectroscopy analysis in that the person from whom the alveolar air, that is the air from the actual lung, is to be investigated, is made to inflate a collecting pouch holding about 1 ltr.

Prior to being introduced into the ion source of the mass-spectrometer, the breath sample must be prepared physically. So far and illustratively this has been done using a cold-trap. The respiratory air to be analyzed first arrives at a trap cooled with frozen methanol wherein the water vapor is frozen out and then this air passes into a second trap cooled with liquid nitrogen where the carbon dioxide is frozen out. At this location the gas components that did not freeze, in particular nitrogen, oxygen and noble gases, are removed using a vacuum pump. Next the second cold trap is heated to allow the frozen carbon dioxide to evaporate, and it is then moved through an intake system into the ion source of mass spectrometer.

Especially with respect to routine use on a large scale, the above described method of sampling, storage and preparation incurs substantial drawbacks:

- Sampling entails a substantial risk of handling errors.
- Only a small quantity of air representing a fraction of the exhalation is sampled; however, the marked carbon dioxide does not necessarily accumulate in the lung in a uniform manner in time and space; in this respect the above method fails to be integrating.
- Even though only one random sample has been taken, the sample vessel of 50 ml remains fairly large; this entails space problems if, for instance, eight samples are taken per patient and at the same time samples from several patients must be shipped and stored.
- The system requires liquid nitrogen which as a rule is unavailable in medical labs and therefore entails special costs of operation.
- The system of cold traps demands careful maintenance and is not easily automated; ice formation at different sites makes is susceptible to malfunctions; in the event of malfunction, the entire analytical the system of cold traps is capital-intensive.
- Sample preparation is time-consuming.

SUMMARY OF THE INVENTION

The method of the invention is especially advantageous when the approximate composition of a gas mixture is known by its classes of substances and if the fractionating of the gas mixture facilitates the ensuing detection or makes it possible at all or if a special gas component is to be separated for further analysis, for instance to determine isotope ratios.

The separation of a weakly adsorbed component from a mixture of more intensely adsorbed components by means of two beds of adsorbents is possible even when these beds are the same material and the pressures and temperatures are equal. Appropriately, the bed crossed first must be so sized in relation to the quantity of the gas mixture that only the weakly adsorbed component continues to flow to the second bed. More or less all components are adsorbed in the first bed, however, the component to be separated is adsorbed only to a slight degree. This component, on the other hand, is adsorbed in the second bed where it is present in its pure form.

As a rule, that gas component associated with one bed but flowing farther will interfere by displacement desorption with the adsorption in the next bed. A portion of the gas component already adsorbed in the bed is replaced by the gas component associated with the previous bed and thereby the intended separation of the gas components is partly negated. Accordingly, the invention proposes to so size the individual adsorbent beds with respect to quantity and approximate composition of the gas mixture and adsorbing power for the conditions of temperature and pressure prevailing in the beds that the gas component assigned to one bed shall not flow farther into the next. The quantity of gas is determined illustratively by the pressure and temperature in a reservoir from which this gas mixture is fed to the sequence of beds. Knowing approximately the composition of the gas mixture and from the adsorption isotherms of the adsorbents listed in the literature, the minimum required size of the particular beds is then determined. As a rule at least one gas component shall not be adsorbed, or be adsorbed only slightly, by any of the beds. This gas component then acts simultaneously as a carrier gas for the other components through all the beds.

The highest possible saturation of the adsorbents by the gas component assigned to it is desired for the ensuing desorption preceding analysis. The amount of gas adsorbed per unit weight of adsorbent is determined by the pressure and temperature. The values for the gases and adsorbents most prevalent in practice are found in the literature in the form of adsorption isotherms. The selection of optimal pressures and temperatures depends on the adsorption isotherms of the diverse adsorbents for the gas components to be stored. The pressure, temperature, adsorbent and bed size are selected in such manner that the departure of one gas component from the bed assigned to it into the next is suppressed and that at the same the highest possible saturation is achieved.

If at the standard conditions of 1 bar and 20° C. the desired separation should be unsatisfactory, then the pressure and/or temperature is selected in such manner in relation to the adsorption isotherms that the differential between the strongly adsorbed gas quantity of one kind and the weakly adsorbed gas quantity of the other kind shall be as pronounced as possible.

This differential is especially large if different pressures and temperatures are present at the various beds. In that case inherently identical materials act as if they were different adsorbents. Therefore the pressures and/or temperatures at beds of identical materials are so selected that the lower pressure, or the higher temperature, is reached first.

Beds of different adsorbents are proposed for the implementation of the method of the invention. The beds consist of such adsorbents that strongly adsorb one portion of the components of the gas mixture to be analyzed while not adsorbing, or only weakly, the other portion. Those adsorbents are preferred for which this differential already is pronounced at the standard conditions of 20° C. and 1 bar.

Zeolitic and carbon molecular sieves are especially well suited for the method proposed by the invention. The zeolitic molecular sieves are almost universally applicable. The adsorption properties of molecular sieves are due to the large inner surface, high electrostatic attractions and a screening effect on the molecular scale. In similarity with mechanical sifting screens, they can be ordered into series of increasing mesh sizes in such a way that a specific and minimum mesh size is associated with each gas molecule just passing through it, yet the gas molecule cannot be adsorbed by molecular sieves of lesser mesh sizes. The types of molecular sieves are uniformly and internationally classified by their molecular mesh sizes and crystal types.

The beds are connected in series in such a way that the coarser molecular sieve follows the finer one; illustratively the type sequence of zeolitic molecular sieves is 3A, 4A, 5A, 10X, 13X.

The problem raised by introducing the most saturated possible adsorbents into the desorption system of the analytical apparatus on one hand and on the other by preventing the undesired overflow is solved by the invention in that, except for the last bed, each bed is divided into a first and a second portion, the first portion being saturated by adsorption kinetics and the second portion remaining unsaturated. The second portions are sized in such a way relative to the gas mixture to be analyzed that the gas components associated with the particular beds shall not flow over into the following beds. In a series of beds, there is no danger of trivial overflow. Only the first portions are fed into the analytical apparatus in qualitative analysis.

The invention is elucidated below in relation to an illustrative example, namely that of human or animal breath samples. Nevertheless it must be understood that with suitable selection of known adsorbents and operational parameters such as pressure and temperature, the invention also is applicable to virtually arbitrary gas mixtures. All data relating to numbers and materials as well as the described equipment components are merely illustrative and do not restrict the general scope of the claims.

BRIEF DESCRIPTION OF THE DRAWINGS

The method and apparatus of the invention will be described with reference to the accompanying drawings, which form a part of this disclosure, and wherein:

FIG. 3b is an end elevation, in partial section, of the pressure cell of FIG. 3a;

FIG. 4b is a transverse sectional view along line B—B of FIG. 4a;

FIG. 4c is a transverse sectional view along line A—A of FIG. 4a;

DESCRIPTION OF THE PREFERRED EMBODIMENT

Figure 1A:
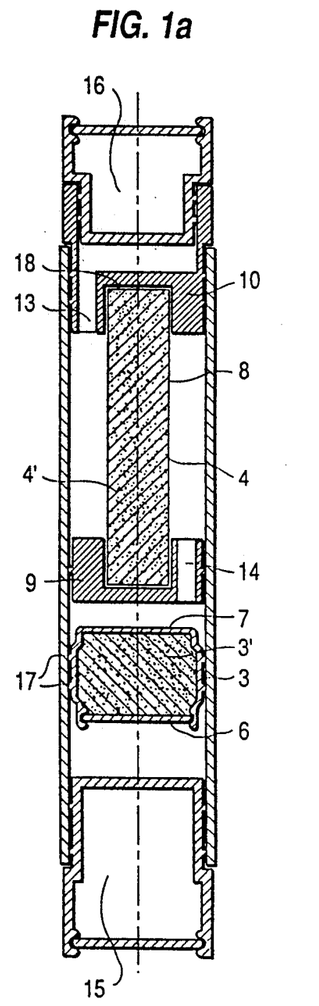
FIG. 1a is a side elevation in longitudinal section of a sampling tube in accordance with the invention in condition for shipping or storage.
Figure 1B:
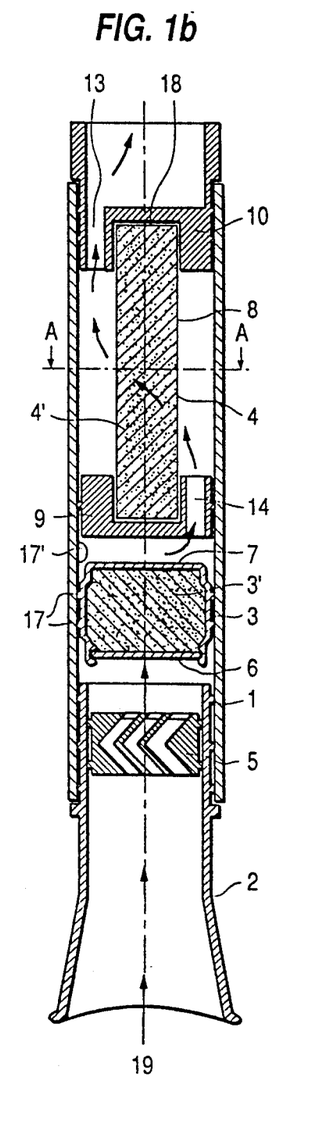
FIG. 1b is a side elevation in longitudinal section of the sampling tube of FIG. 1a in condition for use.
Figure 1C:
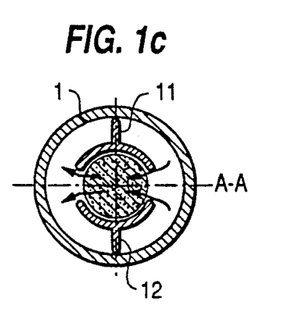
FIG. 1c is a transverse sectional view along line V—V of FIG. 1b.
Figure 1D:
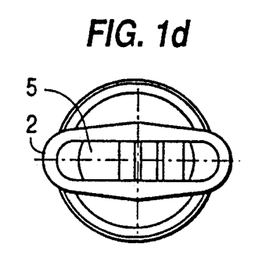
FIG. 1d is an end elevation of FIG. 1b as seen from the bottom of the Figure.
Figure 2:
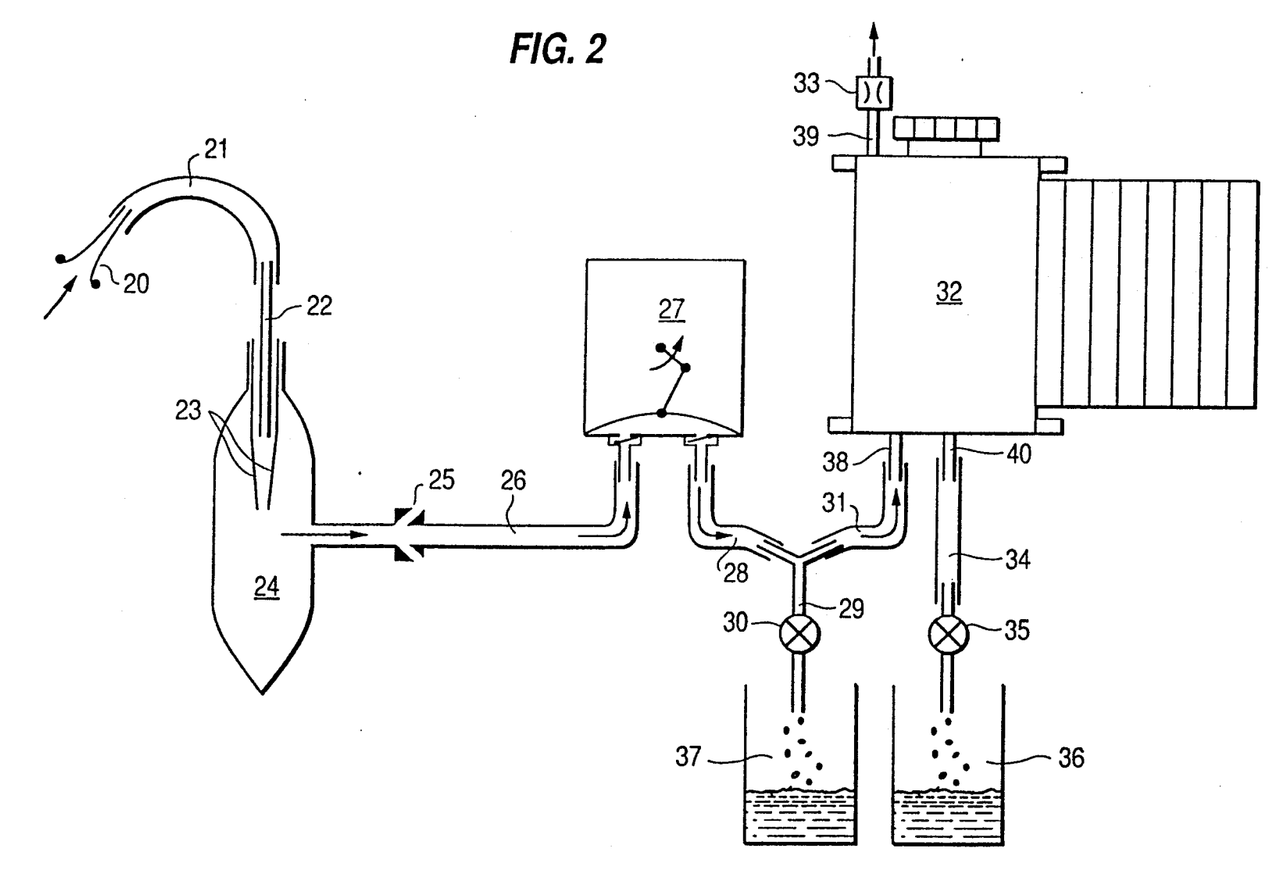
FIG. 2 is a functional schematic view of an apparatus in accordance with the invention showing the gas flow paths therein.
Figure 4A:
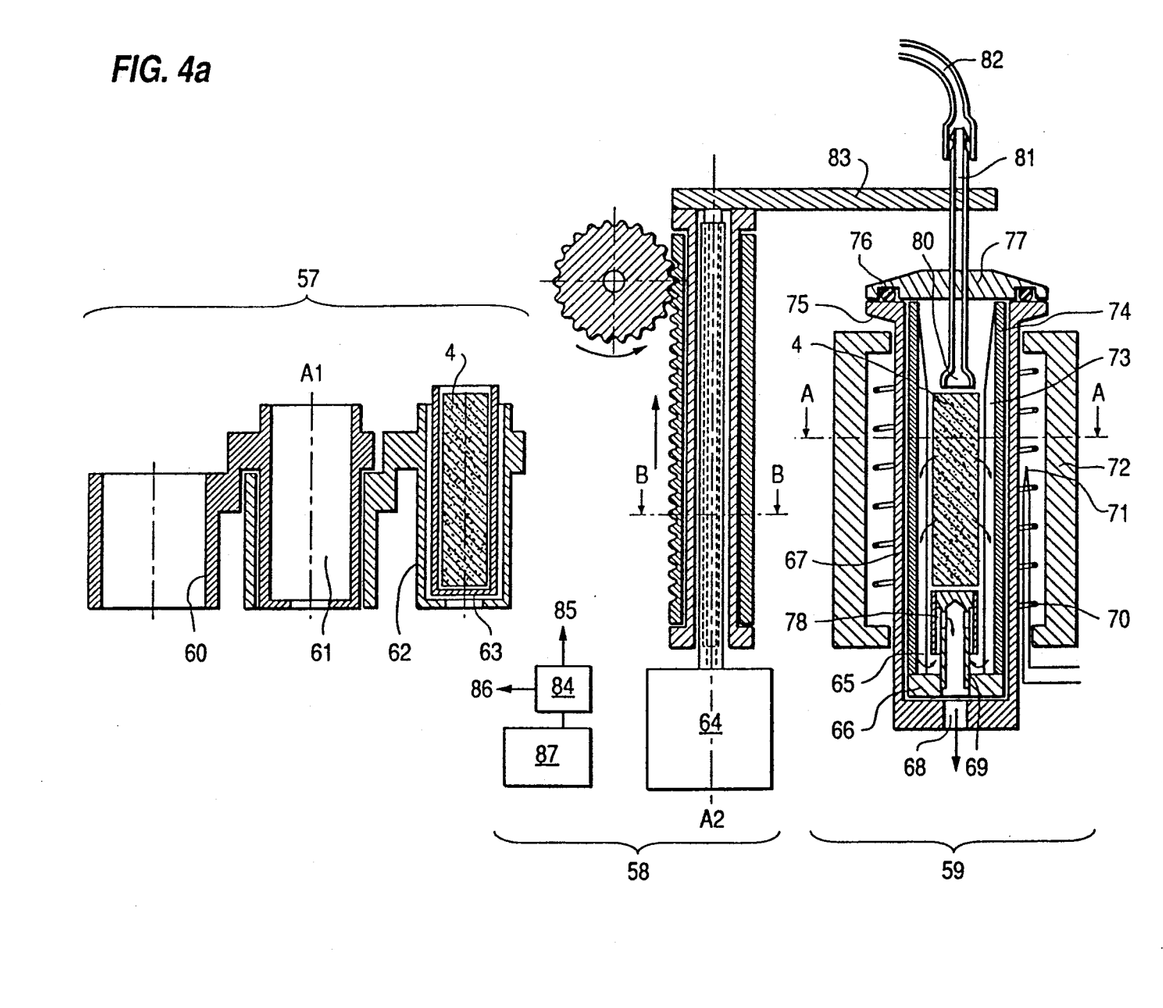
FIG. 4a is a side elevation, in section, of a sample transfer and handling apparatus in accordance with the invention.
Figure 4B:
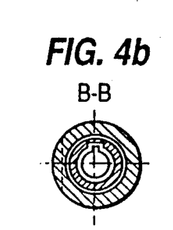
Figure 4C:
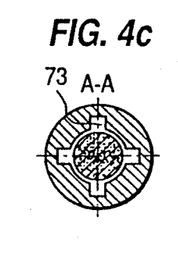
Figure 5:
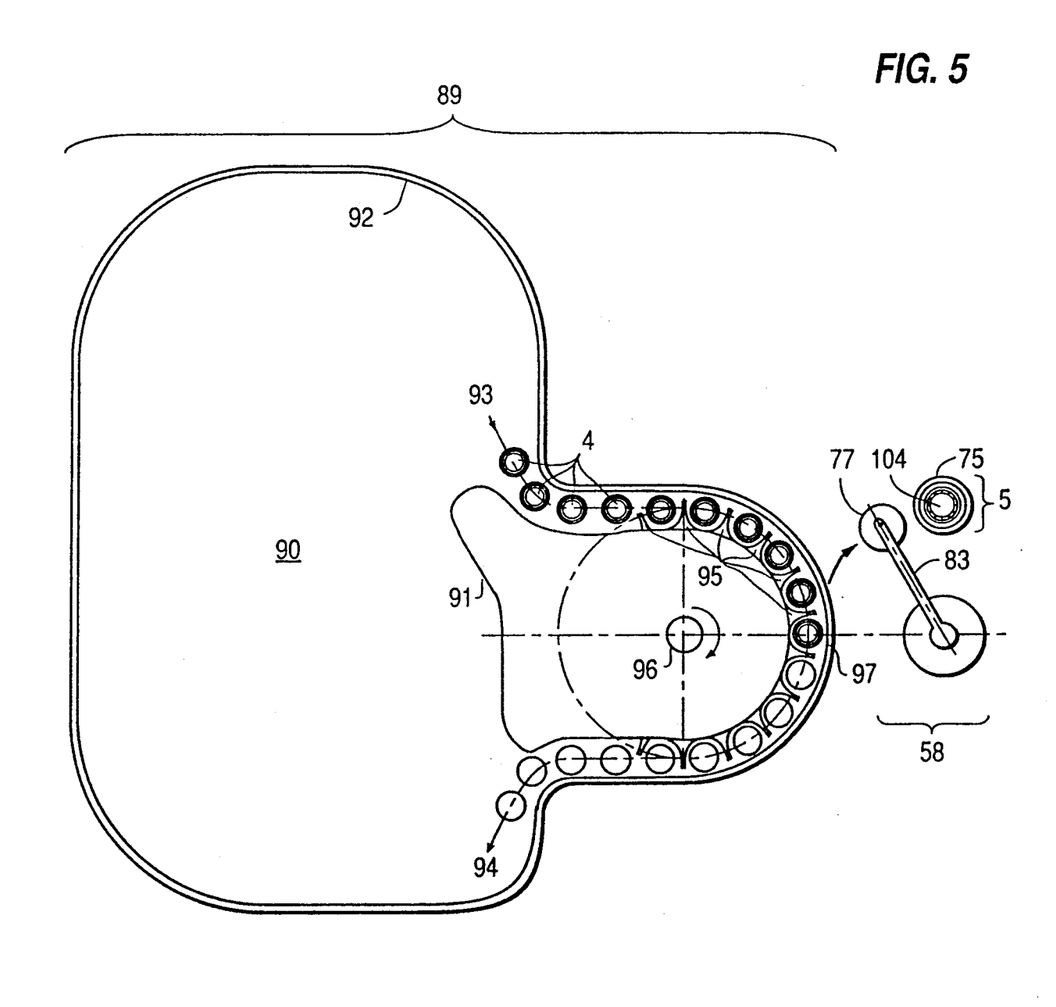
FIG. 5 is an overall schematic diagram of an envelope-magazine system in accordance with the invention.
Figure 6:
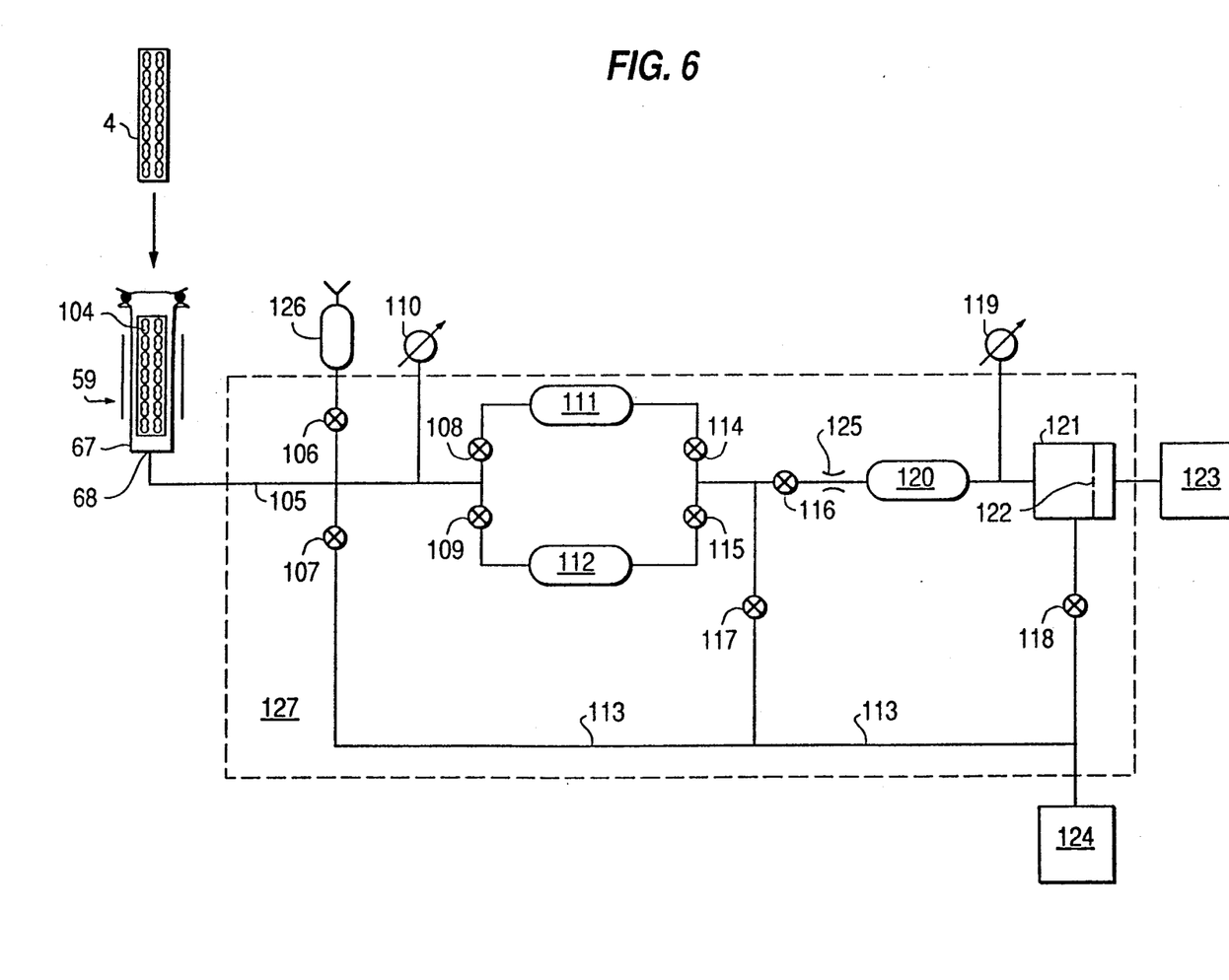
FIG. 6 is a description device using the sampling tube of FIG. 1.

The apparatus units shown in FIGS. 1 through 3 serve to take, store and prepare a respiratory sample. The apparatus units of FIGS. 4 through 6 are used to keep available and to prepare the breath components to be analyzed and directly precede a suitable analytical apparatus. Equipment suitable as analytical apparatus is that illustratively but not exclusively operating on the following principles, namely flame ionization, mass spectroscopy, gas spectroscopy, and optical absorption spectroscopy, especially infrared spectroscopy wherein the light source is a laser and with photo-acoustic detection or designed as differential absorption spectroscopes or as Fourier-Transform infrared spectroscopes. The invention recommends in particular a mass spectrometer or a Fourier-Transform infrared spectrometer.

The apparatus components shown in FIGS. 1 through 3 are units which may be kept apart in space and time from the apparatus components of FIGS. 4 through 6. Because of the independence of sampling and analysis, distributed sampling is made possible, that is, several sampling stations may feed one analytical station. As a result, substantial, economical use is made of the comparatively expensive analytical station.

FIG. 1 is made up of the partial FIGS. 1a, 1b, 1c and 1d. FIG. 1a shows the assembly of a sampling tube in the shipping and storage state. FIG. 1b shows said tube in the operational state. FIG. 1c shows a cross-section of the sampling tube at the site A—A and FIG. 1d shows the tube in the direction of the arrow 19 of FIG. 1b.

The adsorbents provided for desorption in the intake system 127 of the analytical apparatus are filled into gas-permeable envelopes. As a rule adsorbents are powdery or in the form of small particles a few mm in size, which are not easily handled. Because the desorption temperatures can rise to 500° C., the envelope 4 preferably is made of high-purity metallic materials, preferably pure aluminum or pure nickel. The purity of the metallic materials ensures that no gaseous contaminations are released at the desorption temperatures from the envelope material. By imbedding in envelopes of preferably uniform formats, the adsorbents can be handled in the manner of mechanical objects, especially automatically.

After removing gas-tight sealing caps 15 and 16, a mouthpiece 2 is inserted into the support tube 1. It contains a droplet trap 5 which prevents the penetration of larger 10 water-containing droplets into the downstream portion. This is important as otherwise the proposed indirect measurement of breath quantity would be partly spurious. The droplet trap 5 shown in FIG. 1b consists of a series of V-shaped ledges that are vertical in the operational position and which are mounted in such a way that a direct flow-through is impossible. The vertical operational position is made obvious by the flat shape of the mouth-side end and by the anatomy of the human mouth. The mouth-piece 2 and the droplet trap 5 illustratively are made of polyethylene. The droplet trap 5 also may assume a shape different from that shown in FIG. 1b.

Seen in the direction of flow, a bed 3' consisting either of economical silica gel adsorbent or of a zeolitic molecular sieve, preferably type 3A, is inside an envelope 3 and is located behind the droplet trap 5. Technical criteria make the molecular sieve with its higher selectivity and higher adsorption of water vapor preferable over the more economical silica gel.

The envelope 3 is cylindrical and comprises screening and surfaces 6 and 7 provided with gas-permeable apertures. Illustratively, envelope 3 is made of polyethylene. The end surface 6 is designed to be a push-in lid installed following filling with the bed 3'.

Several known small indicator balls may be added to the bed 3' to display the degree of water saturation by color changes, or else the bed may consist entirely of indicator balls. The indicator balls illustratively consist of small molecular-sieve spheres impregnated with an indicator substances. By selecting transparent materials for the envelope 3 and the support tube 1, the adsorbent will be visible from the outside. As a result the color change is noticeable, especially between the marking rings 17 which also are visible from the outside, and approximate measurement of the quantity of respiratory air is thus possible. The suggested indicator substance is cobalt-II-chloride, which upon water absorption forms a hexaqua complex and thereby changes its color from blue to pink.

Water-vapor adsorption by the molecular sieve of the bed 3' is strongly exothermic. If sampling is rapid, the heat of reaction cannot be dissipated into the ambient and the flowing respiratory air heats up so much that the carbon dioxide it contains will be adsorbed only slightly in the next bed 4'. It is suggested therefore with respect to rapid sampling that the first equipment portion comprise a temperature display for the respiratory air leaving the bed 3', preferably in the form of a color speck 17' displaying a color change when a specific temperature has been reached (FIG. 1b) and consisting of a known indicator color, this color change preferably taking place at a temperature at which the carbon dioxide already adsorbed by the bed 4' does not yet desorb. Sampling in such cases then is terminated the moment there is a color change.

A more accurate measurement of respiratory air is made possible by the preferably polyethylene collapsible pouch of the invention to collect the flowing breath and which is mounted into the component 10 instead of the stopper 16.

Preferably the envelope 4 is in the shape of a cylinder with a length/diameter ratio of at least 2/1. Except for the upper and lower rims, the peripheral surface 8 is provided, as much as possible everywhere, with small or narrow, arbitrary apertures (such as slits, circular holes, elongated slots or scale-shaped orifices) in such a manner that spheres about 0.8 mm in diameter cannot escape from the envelope. The envelope 4 provided for purposes of desorption comprises at least one smooth end face 18 to which can be applied a vacuum suction cup 80 (FIG. 4). Preferably the envelope 4 consists of pure aluminum or pure nickel, and the bed 4' of a zeolitic molecular sieve.

The molecular-sieve bed 4' inside the envelope 4 is crossed by the flow transversely to the cylinder axis. The advantage of low flow impedance both for the adsorption and for the later desorption is achieved thereby. This cross-flow is achieved by suitably dividing the support tube internal diameter The support-tube segment bounded by the transverse bulkhead walls 9 and 10 is divided into two mutually sealed longitudinal halves by the longitudinal bulkhead walls 11 and 12. The transverse bulkhead walls 9 and 10 comprise gas-transmitting apertures 13 and 14 and furthermore seating boreholes for the envelope 4. The longitudinal bulkheads 11 and 12 are extended by fins resting in geometrically locking manner against the surface 8 of the envelope 4 outside the inflow and outflow zones. The overall assembly consisting of the components 4, 9, 10, 11 and 12 amounts so to speak to a push-in stopper easily pulled out of the support tube 1. It can be easily disassembled without tools to remove the envelope 4.

FIG. 2 schematically shows an apparatus of the invention. The collapsible pouch 24 is filled with respiratory air through the mouthpiece 20, the connection hose 21 and the hose hookup tube 22. A check valve consisting of two floppy foils 23 prevents the respiratory air from back-flowing during the inflation. The collapsible pouch 24 can hold about 5 ltr and is connected through the conical quick-disconnect connector 25, allowing easy exchange to the connection hose 26 to the membrane compressor 27. The membrane compressor 27 is suspended with its head down to allow condensation water separated from the respiratory air to drain through the pressure-side connection hose 28. The condensation water is separated at the Y-connector 29 from the compressed air which passes through the connection hose 31 to the pressure cell 32. Periodically the water is drained through the valve 30 into a collection vessel 37. Flow and pressure are adjusted by the throttle 33. A timer switch not shown determines the time of operation of the membrane compressor 27 and hence the amount of conveyed air.

The components 27, 32, 33 are predominantly metallic. All other components may be made for instance of polyethylene. The hose hookup tube 22 illustratively is made of polyethylene with approximately a 10 mm diameter and 1 mm wall-thickness and is thermoplastically welded to the polyethylene-foil components 23 and 24.

Figure 3A:
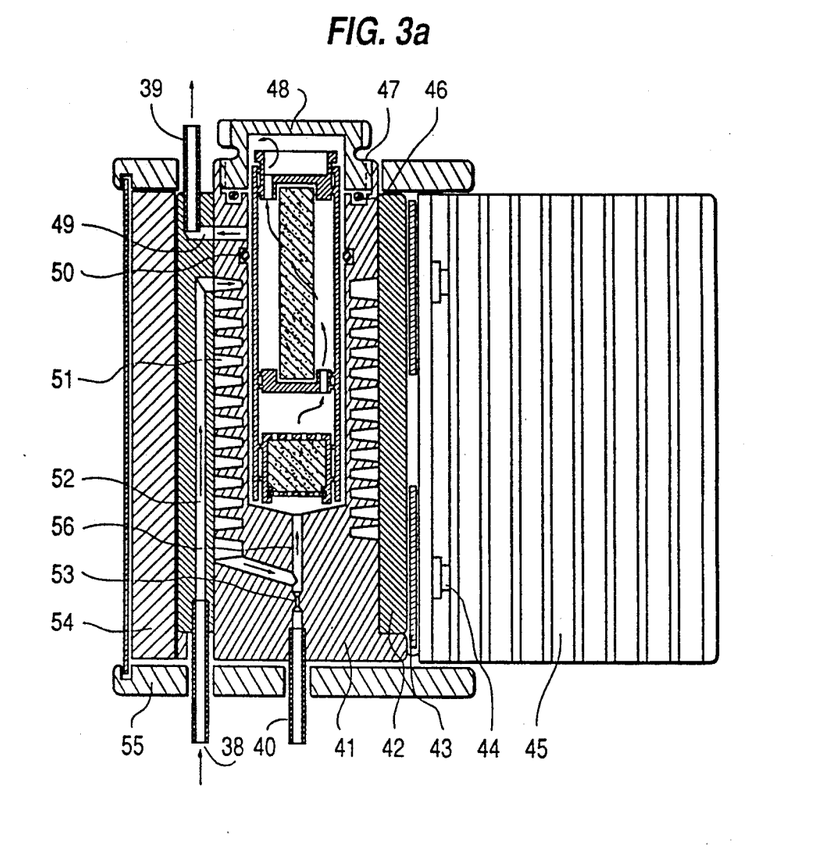
FIG. 3a is a side elevation, in section, of a pressure cell in accordance with the invention.
Figure 3B:
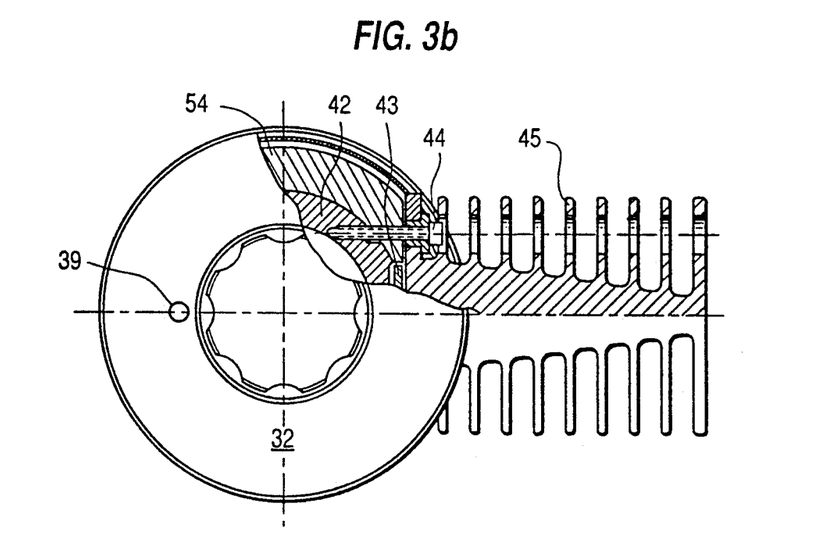

The pressure cell 32 is shown in detail in FIG. 3. The outer cylinder 42 encloses tightly the threaded inner cylinder 41, whereby the helical cooling duct 51 is formed. The outer cylinder is the location for the air intake conduit 52 connected through the intake stub 38 to the connection hose 31 to the membrane compressor 27 and the exhaust air conduit 49 issues into the exhaust air stub 39. The screws 44 tighten together the outer cylinder 42, the Peltier elements 43 and the radiator 45. Thermal insulating layers 54 and 55 increase the temperature gradient between the ambient and the outer cylinder 42, the Peltier elements 43 sustaining the heat flow from the outer cylinder 42 to the radiator 45.

The inner cylinder 41 comprises a central borehole to receive the support tube 1 as in FIG. 1b, including the above described components except the mouthpiece 2. The envelope 4 may be filled with a carbon molecular sieve. Together with its contents, the support tube 1 is moved through the aperture of the threaded seal 48, of which the thread is denoted by 47, into the central borehole of the inner cylinder 41, or is removed from it in that manner. The 0-ring 46 acts as a seal to build up the pressure throughout the entire system from the membrane compressor 27 to the throttle 33. The 0-ring seal 50 prevents flow bypass between the inflow orifice 56 and the exhaust air duct 49 and constrains flow through the envelopes 3 and 4 in the direction of the arrows. The water condensing in the cooling duct 51 can drain through the capillaries 53 into the drain stub 40 from which it is periodically drained through the connection hose 34 and the valve 35 into the collection vessel 36.

FIG. 4 shows a segment of two links 60 and 62 of a sample conveyor chain 57, a sample transfer device 58 and a desorption device 59. As shown by FIG. 5, the envelopes 4 charged with gas samples are sequentially moved by the sample transfer device 58 into the desorption device 59. Up to several hundred chain links can be hooked up together, so that the sample conveyor chain can be loaded with as many sample envelopes.

The mutually gripping chain links 60 and 62 move about a common axis of rotation A1. The cylindrical cavity 61 may receive a cylindrical secondary vessel 63 containing an envelope 4 with a gas sample. Correspondingly the secondary vessel 63 may be sealed gas-tight by a stopper, not shown, and serve as a conveyor vessel for the sample sleeve 4 between the sampling site and the analytical apparatus. The arm 83 of the sample transfer device 58 carries out a lifting motion and a rotation about the axis A2 by means of known drive elements shown in FIG. 4. The motor implementing the rotation is denoted by 64.

The sample transfer device 58 comprises an arm 83 with a suction-gripper. This gripper illustratively comprises a tube 81 with a suction-cup 80 at its lower end. The other end of the tube 81 is connected through the hose 82 with the intake 85 of the valve 84 which in turn is hooked-up to the vacuum pump 87. During the actual conveyance process, the vacuum is applied by the valve 84 to the suction gripper and when the envelope 4 is released, the vacuum is turned off by venting the intake 86. The transfer device 58 moreover comprises an arm 83 to which is affixed a lid 77 with a sealing ring 76 to seal the desorption container 67 vacuum-tight. However, the lid 77 is not necessarily integral with the suction gripper 80,81 in the manner shown by FIG. 4.

The desorption device 59 consists of the vacuum vessel 67, the vessel inset 74 and the heater system 70,71,72. The vacuum vessel 67 consists of a tube at the upper end of which is located the flange 75 and to the lower end of which is mounted the tube fitting 68 to hook up to the intake system 127 of the analytical apparatus. In the embodiment shown in FIG. 4, the vacuum vessel 67 is enclosed on the outside by the heater coil 70, the temperature sensor 71 and the thermal insulating jacket 72. In a different embodiment, the heater system can be located inside the vacuum vessel 67.

The vessel inset 74 consists of a pipe of which the lower end is closed by the plate 66. The inside wall of the vessel inset 74 comprises longitudinal flutes 73 allowing the desorbed gas to flow away. The vessel inset 74 is easily removed from the vacuum vessel 67 when required for cleaning and maintenance.

The tube fitting 68 is protected by a device against the penetration of dropping particles, for instance from the molecular sieve. As shown in the embodiment of FIG. 4, this protective device consists of the pipe stub 69 mounted in the plate 66 and of which the upper intake apertures 65 are covered by a cap 78 which is pulled far down on the side. The protective cap 78 at the same time serves as a rest for the sample envelope 4.

In another embodiment, a particle filter may be used to solve the problem of preventing penetration of particles.

FIG. 5 shows the envelope-magazine system 89 together with the sample transfer device 58 and the desorption device 59 of FIG. 4. In this embodiment the magazine consists of a bench 90 which can receive up to several hundred sample envelopes 4 in a corresponding number of secondary vessels 63 and chain links 60, 62, and further it includes a sprocket wheel 95/96 and the guide means 91 and 92. 95 denotes the tooth and 96 the shaft of a sprocket wheel driven by a motor, not shown. During rotation of the sprocket wheel, the guide means 91 and 92 sequentially move the chain links laden with the sample envelopes 4 to the transfer position 97. 93 denotes the chain entry and 94 the chain exit.

The unit shown in FIG. 6 is a desorption device 59 with an intake system 127 connected to an analytical apparatus 123. The analytical apparatus should be an instrument for the isotope ratio measurement, in particular a mass spectrometer or a Fourier-Transform infrared spectrometer. Illustratively, the mass spectrometer may be a magnetic zone instrument with several ion collectors to determine the isotope ratios, or alternatively, it can be a so-called quadrupole mass spectrometer.

Essentially the intake system 127 includes a system of gas vessels tightly sealed relative to the ambient and interconnected by pipes and valves. The system may be evacuated in part or in whole by a vacuum pump 124 and can be monitored by the pressure pickups 110 and 119. The expression pressure pickups covers also vacuum measuring instruments. All pressures cited below are absolute. The expression gas vessel also covers pipe segments sealed by the valves.

In FIG. 6, the envelope 4 contains an adsorbent 4' laden with a gas sample; envelope 4 is outside the system that is sealed gas-tight. 104 denotes such an envelope inside the desorption vessel 67 shown in FIG. 4. The connection pipe 105 is hooked up to the pipe fitting 68 and leads from the desorption vessel 67 to the remaining system. The numerals 106, 107, 108, 109, 114, 115, 116, 117 and 118 denote valves; the numerals 111, 112 and 120 denote gas vessels which also may be formed by pipe segments.

The pressure-reducing stage 121 reduces the pressure of the gas to be analyzed from the comparatively high pressure of about 100 mbars in the vessel 120 to the low pressure of about 0.0001 mbars in the ion source of the mass spectrometer 123, that is, the pressure drops by about 6 orders of magnitude. This pressure reduction is achieved by means of high flow impedance 122, for instance a narrow aperture in a gold foil or a flake of tightly sintered high-grade steel powder. If another analytical apparatus is used than the mass spectrometer 123 cited in this illustrative embodiment, for instance a Fourier-Transform infrared spectrometer, then the pressure reduction may be of another magnitude or may be omitted entirely.

The vacuum pump 124 may be a rotary vane pump and through the pump line 113 and the valves 107, 117 and 118 can access the various segments of the intake system 127. Illustratively, the piping consists of high-grade steel pipes with inside diameters of about 5 to 10 mm. Preferably the inside surfaces are electrolytically burnished or coated with teflon so that impurities or residues from previous gas samples do not adhere to the inside walls. For the same reason the entire system shown in FIG. 6, except for the equipment 59, 123, 124, 126 and 113 integrated into a heated box 127 shown in dashed lines, is kept at a temperature preferably higher than 80° C. For the sake of rapid gas changes, the gas intake system is operated preferably in the laminar flow range at pressures especially above 1 mbar. When being internally cleaned, the entire system beginning with the filter 126 can be flushed with pure, dry air, the lid 77, the valves 107 and 117 being closed and all other valves being open. Illustratively, the filter 126 may be a bed of zeolitic molecular sieve and a subsequent bed of activated charcoal.

The pickups of the pressure measuring instruments 110 and 119 operate for instance with piezoelectric elements. The valves 106, 107, 108, 109, 114, 115, 116, 117 and 118 may be in the form of electromagnetic valves. The electrical power supplies and electronic control units which are part of the second portion of the apparatus are known per se. A process computer supports the control of the method steps discussed below.

Presently the method steps of the invention will be discussed in relation to the above described apparatus and by the example of a concrete diagnostic problem, where the isotope ratio is demanded for the exhaled carbon dioxide of a patient who received a diagnostic drug.

The patient blows his breath through the mouthpiece (FIGS. 1b, 1d) into the bed 3' of the molecular sieve until about half the indicator spheres display a color change. The color change zone then is located between the marking rings 17 present on the envelope 3. At standard conditions of 20° C. and 1 bar, only the water vapor contained in the exhaled air shall be adsorbed by this bed. Thereupon the respiratory air arrives in the molecular sieve bed 4'. This molecular sieve bed 4' adsorbs both the water vapor and the carbon dioxide contained in the respiratory air. Water vapor can be adsorbed preferentially and even is able to displace carbon dioxide that was already adsorbed. The bed 3' preceding the bed 4' however is so sized in the invention that it can accept all the water vapor contained in the respiratory air before this respiratory enters the bed 4'.

A respiratory quantity of 5 ltr is delivered by one person in about 2 to 4 exhalations. This quantity of air contains about 0.1 g water and 0.4 g carbon dioxide. Under standard conditions, the 3A molecular sieve can store about a fifth of its own weight of water and about one tenth of its own weight of carbon dioxide. An amount of about 1 g of 3A molecular sieve therefore is quite sufficient to dehydrate 5 ltr of respiratory air with adequate reliability without the bed 3' being water-saturated. In the invention the quantity of the bed 4' is made such that the molecular sieve is well saturated with carbon dioxide, that is, the molecular sieve should be kept within 2 to 3 g for 5 ltr of respiratory air. Saturation is displayed indirectly by a color change in about half the indicator spheres in the envelope 3 responding to the water vapor contained in the breath. In the invention the bed 3' is of such size that it is saturated only half with water vapor when the bed 4' is fully saturated with carbon dioxide.

Once the bed 4' has been saturated with carbon dioxide by a sufficient number of exhalations, the envelope 4 is removed from the apparatus component of FIG. 1 and placed in a transport or secondary vessel 63 as shown in FIG. 4. If analysis takes place immediately upon sampling, the secondary vessel 63 is directly loaded into the conveyor chain 57. Otherwise the secondary vessel 63 is sealed airtight by a stopper until it will be analyzed.

The further course of the method is described in relation to FIGS. 4, 5 and 6. The released envelope 4 is inside the secondary vessel 63. The other links of the conveyor chain 57 also may be loaded in the same manner. In the same way as later for the other envelopes, the envelope 4 is sequentially transferred at the transfer position 97 from the sample transfer device 58 and moved into the desorption device 59.

The object of the next method step is to transfer the gas stored inside the envelope 4 on the molecular-sieve bed 4' into the vessel 111 while keeping the gas as free as possible from contamination, the vessel 111 being sealed by the valves 108 and 114. Prior to filling, the vessel 111 is evacuated through the opened valves 114 and 117 and through the pump line 113 by means of the constantly operating pump 124 down to a vacuum of about 0.1 mbar absolute. Thereafter, the valve 114 is closed again.

Before opening the lid 77, the desorption vessel 67 must be flooded to ambient pressure. This is accomplished by opening the valve 106 while the valves 107, 108 and 109 remain closed. Pressure balance takes place through the filter 126 and by monitoring the pressure meter instrument 110.

After the pressure meter instrument 110 has displayed the pressure balance, the lid 77 is raised off the desorption vessel 67 and the envelope 4 loaded with the molecular-sieve bed 4' is moved into the desorption vessel 67. The desorption vessel 67 is connected through the valve 107 and the pump line 113 with the constantly running pump 124 and is evacuated down to a specific pressure of about 20 mbars absolute. The purpose of this step is to immediately evacuate any contamination before such would further enter the intake system 127. As soon as the specified pressure has been reached, the valve 107 is closed and valve 108 is opened. Because of the heat transfer from the wall of the desorption vessel 67 constantly heated to about 100° to 200° C. toward the molecular sieve bed 4' in the envelope 104, this bed begins to rise in temperature. As a result the gas stored on the molecular sieve is desorbed and passes through the opened valve 108 into the vessel 111.

Once the pressure measured by the pressure instrument 110 has risen to a pre-specified value of about 1 bar, the valve 108 is closed. The gas that previously had been stored on the molecular sieve in the envelope 104 now has been collected predominantly in the gas vessel 111 between the valves 108 and 114.

In the next method step, the gas to be analyzed is transferred from the vessel 111 into the vessel 120 from where it then passes through the pressure reducing stage 121 into the ion source of the mass spectrometer 123. The temporarily collected gas between the valves 116 and 118 is at rest during analysis, which consumes only a negligible amount of gas. This state of rest assures a constant pressure, which is especially demanded in high-precision measurements, in the measuring cell of the analytical apparatus.

The transfer of the gas from the vessel 111 into the vessel 120 takes place in the following stages. First the volume between the valves 116 and 118, with valve 116 closed and valve 118 open, is evacuated by the pump 124 to about 0.1 mbars. Then valve 118 is closed and valves 114 and 116 are opened. The gas then begins to flow out of the vessel 111 and into the vessel 120 until the pressure sensed by the pressure instrument 119 reaches a specified value of about 100 mbars, whereupon both valves 114 and 116 are closed. The throttle 125 delays the flow transfer to such an extent that all switching elements can follow in time. This ensures that the specified pressure value is set within specified tolerances in the gas vessel 120. The supply of gas stored in the vessel 111 is sufficient to repeatedly fill the vessel 120, and measurements of the same gas can be repeated correspondingly often.

A second gas sample is then transferred from a second envelope 4 or 104 into the gas vessel 112. This procedure is similar to that described for the first sample, and so is the transfer of the second sample from the gas vessel 112 into the gas vessel 120, in which case the second sample is measured. In this manner the first and second samples can be immediately compared to one another in a so-called sample-reference measurement or sample-standard measurement.

The transfer of a second gas sample into the gas vessel 112 can take place simultaneously with the measurement of a first gas sample. Sequentially third, fourth, fifth etc. gas samples can be transferred into the gas vessel 112 and be measured alternatingly with the first gas sample. In this manner immediate comparison of all second and ensuing gas samples can be made with the first gas sample.

As a result, regarding the diagnostic problem mentioned in the illustrative embodiment, the time-function of the isotope ratio in the exhaled carbon dioxide can be determined. Following administration of the test substance, one respiratory sample is taken from the tested person at given time intervals.

In the event the first gas sample need not be retained, gas samples may be transferred alternatingly into the gas vessels 111 and 112 or the gas vessel 112 may be eliminated entirely.

I claim:

1. A method for determining an isotope ratio in exhaled $CO_2$ in a breath sample comprising the steps of
   at a sampling site, blowing respiratory air sequentially through at least one fixed bed of adsorbent for adsorbing water vapor and one fixed bed for adsorbing $CO_2$,
   moving the bed for adsorbing $CO_2$ from the sampling site to a testing site;
   at the testing site, desorbing the $CO_2$ by heating, and analyzing the desorbed $CO_2$ for isotope ratios therein.

2. A method according to claim 1 wherein the step of desorption also includes lowering the pressure of the bed.

3. A method according to claim 2 wherein desorption includes
   first pumping the pressure of the bed down to about 20 millibars,
   discarding desorbate pumped off during the first pumping,
   pumping down the bed to a lower pressure, and
   wherein the step of analyzing includes analyzing the desorbate obtained only during the last pumping down.

4. A method according to claim 3 wherein the step of analyzing includes analysis by one of mass spectroscopy or infrared spectroscopy with photo-acoustic substantiation.

5. A method according to claim 1 wherein in the step of analyzing the desorbate is fed in laminar flow to analyzing apparatus at a pressure greater than 1 mbar.

6. A method according to claim 1 wherein the step of moving is preceded by sealing the adsorbent bed to be analyzed in a gas-tight sealed container for transportation from the sampling site to the testing site.

7. A method according to claim 1 wherein both test beds consist of the same material.

8. A method for determining an isotope ratio in exhaled $CO_2$ in a breath sample comprising the steps of
   at a sampling site, blowing respiratory air sequentially through at least one fixed bed of adsorbent for adsorbing water vapor and one fixed bed for adsorbing $CO_2$,
   moving the bed for adsorbing $CO_2$ from the sampling site to a testing site;
   at the testing site, desorbing the $CO_2$ by lowering the pressure of the bed, and
   analyzing the desorbed $CO_2$ for isotope ratios therein.

9. A method according to claim 8 wherein the step of desorption also includes heating the bed.

10. A method according to claim 9 wherein desorption includes
    first pumping the pressure of the bed down to about 20 mbars,
    discarding desorbate pumped off during the first pumping,
    pumping down the bed to a lower pressure, and
    wherein the step of analyzing includes analyzing the desorbate obtained only during the last pumping down.

11. A method according to claim 10 wherein the step of analyzing includes analysis by one of mass spectroscopy or infrared spectroscopy with photo-acoustic substantiation.

12. A method according to claim 8 wherein in the step of analyzing the desorbate is fed in laminar flow to analyzing apparatus at a pressure greater than 1 mbar.

13. A method according to claim 8 wherein the step of moving is preceded by sealing the adsorbent bed to be analyzed in a gas-tight sealed container for transportation from the sampling site to the testing site.

14. A method according to claim 8 wherein both test beds consist of the same material.

15. An apparatus for collecting a sample of exhaled breath for subsequent analysis to determine the isotope ratio in exhaled $CO_2$ in the breath comprising the combination of
    a first housing having a gas intake orifice and a gas discharge orifice;
    first and second adsorbent beds mounted in said housing for gas flow therethrough in sequence in a direction of gas flow from said inlet orifice to said outlet orifice;
    said first adsorbent bed receiving gas first from said inlet orifice and including a first material for adsorbing water vapor carried in said gas; and
    said second bed including a second material for adsorbing $CO_2$ from said gas.

16. An apparatus according to claim 15 wherein said first and second materials are chemically the same as each other.

17. An apparatus according to claim 15 wherein said beds are removable from said housing.

18. An apparatus according to claim 15 wherein said housing comprises and elongated, cylindrical tube having a gas intake orifice at one longitudinal end.

19. An apparatus according to claim 15 and further comprising first and second gas permeable sleeves for receiving and supporting said beds.

20. An apparatus according to claim 19 wherein one of said gas permeable sleeves includes surface apertures and is mounted in said tube so that gas enters said sleeve in a direction transverse to a central axis of said tube.

21. An apparatus according to claim 15 and further comprising a gas-impermeable pouch having an intake opening attached to said outlet orifice of said tube.

22. An apparatus according to claim 15 wherein said adsorbing material is zeolite.

23. An apparatus according to claim 15 wherein said adsorbing material comprises at least one carbon-molecular sieve.

24. An apparatus according to claim 23 wherein said beds include sieves of increasing molecular mesh sizes in the direction of gas flow.

* * * * *